United States Patent [19]

Zurawski et al.

[11] Patent Number: 5,017,692
[45] Date of Patent: May 21, 1991

[54] TRUNCATED HUMAN INTERLEUKIN-A ALPHA

[75] Inventors: Gerard Zurawski; Sandra M. Zurawski, both of Redwood City, Calif.

[73] Assignee: Schering Corporation, Kenilworth, N.J.

[21] Appl. No.: 903,497

[22] Filed: Sep. 4, 1986

[51] Int. Cl.$^5$ ............... C07K 13/00; C12P 21/06; C12P 19/34; C12N 15/00; C12N 1/22; C07H 15/12

[52] U.S. Cl. ............... 530/351; 435/69.52; 435/91; 435/172.3; 435/252.33; 536/27; 935/19; 935/29; 935/41; 935/56; 935/61; 935/73; 935/81

[58] Field of Search ............... 435/68, 70, 91, 172.1, 435/172.3, 69.1, 320; 530/351

[56] References Cited

U.S. PATENT DOCUMENTS 4,571,421  2/1986  Itakura ............... 536/27
4,695,623  9/1987  Stabinsky ............... 435/68

FOREIGN PATENT DOCUMENTS 0136489  4/1985  European Pat. Off. .
85/02200  5/1985  World Int. Prop. O. .

OTHER PUBLICATIONS

Mullenbach et al., "Chemical Synthesis and Expression in Yeast of a Gene Encoding Connective Tissue Activating Peptide III . . . Mitogen", *The Journal of Biological Chemistry*, vol. 261, pp. 719–722 (1986).

Itakura, K. & Riggs, A., "Chemical DNA Synthesis and Recombinant DNA Studies", *Science*, vol. 209, pp. 1401–1405.

Wells et al., "Cassette Mutagenesis: and Efficient Method for Generation of Multiple Mutations at Defined Sites", *Gene*, vol. 34, pp. 315–323 (1985).

Estell et al., "Probing Steric and Hydrophobic Effects on Enzume–Substrate Interations by Protein Engineering", *Science*, vol. 233, pp. 659–663 (1986).

Porter et al., "Novel Modified Beta–Interferons: Gene Cloning, Expression, and Biogical Activity in Bacterial Extracts", *DNA*, vol. 5, pp. 137–148 (1986).

Sproat, B., and Gait, M., "Chemical Synthesis of a Gene for Somatomedin C", *Nucleic Acids Research*, vol. 13, pp. 2959–2977 (1985).

Ferretti et al., "Total Synthesis of a Gene for Bovine Rhodopsin", *Proc. Natl. Acad. Sci.*, vol. 83, pp. 559–603 (1986).

Marx, J., Article: "Interleukin–1 Genes are Cloned, the cloning work indicates that there is a family of interlukin–1 proteins . . . might work", *Science Research News*, vol. 22, pp. 1076–1077 (1985).

Webb et al., "The Molecular Cloning of Human Interleukin–1 Precursor cDNA and its Expression in Monkey Cells", *Cellular and Molecular Biology of Lymphokines* (No Volume number), pp. 685–695 (1985).

Gubler et al., "Recombinant Human Interleukin 1 alpha: Purification and Biological Characterization", *The Journal of Immunology*, vol. 136, pp. 2492–2497 (1986).

March et al., "Cloning, Sequence and Expression of Two Distinct Human Interleukin–1 Complementary DNAs", *Nature*, vol. 315, pp. 641–647 (1985).

*Primary Examiner*—Robin L. Teskin
*Assistant Examiner*—Joan Ellis
*Attorney, Agent, or Firm*—Stephen C. Macevicz

[57] ABSTRACT

Synthetic human interleukin-1α genes are provided whose codons are selected from those preferred by bacteria. High expression levels are obtained in an *E. coli* expression system for both native interleukin-1α and several mutant interleukin-1α's.

1 Claim, 9 Drawing Sheets

```
EcoRI
AATTCTCATGTTGACAGTTATCTCGGAGCTGCATGTGTCAGAGCTTTCACCGTCATCACCGAAACG
    GAGTACAACTGTCGAATAGAGCCTCGACGTACACAGTCTCGAAAGTGGCAGTAGTGGCTTTGC
              10        20        30        40        50        60
                                         tacP CGGCAGGCAAGCTGTTGACAATTAATCATCGGCTCGTATAATGTGTGGAATTGTGAGCGGATAACAATTTCA
GCCGTCCGTTCGACAACTGTTAATTAGTAGCCGAGCATATTACACACCTTAACACTCGCCTATTGTTAAAGT
  70        80        90       100       110       120       130
                       RBS         MET      synthetics 1A/B
CACAGGAAACAGGATCGTAAGGAGGTTAACATG  TCTGCACCGTTCAGCTTCCTGAGCAACGTAAAATA
GTGTCCTTTGTCCTAGCATTCCTCCAATTGTAC  AGACGTGGCAAGTCGAAGGACTCGTTGCATTTTAT
 140       150       160     169            10        20        30
                                            TaqI/AccI  pUC12
CAACTTCATGCGTATCATCAAATACGAATTTATCCTGAACCAAT cgacctgca ....
GTTGAAGTACGCATAGTAGTTTATGCTTAAATAGGACTTGGTTAGC tggacgt ....
   40        50        60        70        80    93
```

FIGURE 1A

```
    MstI         "XbaI"         MstI                   synthetics 5A/B
CGTGATCCTGCGCatc    ctagagcTGGCATCTCTAAAACTCAGCTGTACGTAACTGCTCAGGACGAA
GCACTAGGACGCGTaggatc    tcgACGCGTAGAGATTTTGAGTCGACATGCATTGACGAGTCCTGCTT
        67                     10           20           30           40 synthetics 6A/B
GACCAGCCGGTACTGCT    GAAAGAAATGCCGAAATCCCGAAAACCATCACTGGTTCTGAAAC
CTGGTCGGCCATGACGACTTTCTTTA    CGGGCCTTTAGGGCTTTTGGTAGTGACCAAGACTTTG
        50              60          73         10          20          30

KpnI
CAACCTGCTGTTCTTCTGGGAAACTCACGGTAC
GTTGGACGACAAGAAGACCCTTTGAGTGC
        40                50           65
```

FIGURE 1B

```
pUC12  BamHI    ClaI              synthetics 3A/B
cccggg  gatccat CGATAATCCGTGCTAACGACCAGTACCTGACTGCTGCTGCACAACCTGG
gggccctag       gtaGCTATTAGGCACGATTGCTGGTCATGGACTGACGACGACGTGACGTGTTGGACC
                         10        20        30        40        50 synthetics 4C/D
         GCAGTAAAATTTGACATGGGTGCTTACAAATCTTCTAAAGATGATGCTAAAATCAC
         AAACTGTACCCACGAATGTTTAGAAGATTTCTACTACGATTTTAGTG
                  10        20        30        40

ACGAA
TGCTTCGTCATTTT
      71
   60
```

FIGURE 1C

```
                                       synthetics 7A/B
pUC12   SalI      KpnI
ctctagag  tcgaccGGTACCAAAAACTACTTCACTTCTGTTGCTGCTCACCCGAACCTGTTCATCGCTAC
gagatctcagct    ggCCATGGTTTTTGATGAAGTGAAGACAACGAGTGGGCTTGGACAAGTAGCGATG
                  10          20          30          40          50 synthetics 8A/B
             ACTGGGTTTGCCTGGCAGGTCCGTCTATCACTGACTTCCAGATCC
             CGGACCGTCCAGGCGGCCAGATAGTGACTGAAGGTCTAGG
                     10          20          30          40

BglII   HindIII    pUC12
TAAACAGGACT                   agcttggcactggcc........
ATTTGTCCTGATGACCCAAA          accgtgaccgg........
        60          75

TGGAAAACCAGGCAGATCTA
ACCTTTTGGTCCGTCTAGATTCGA
        50          66
```

```
                                         pUC12
       IL-1
Ile Leu Glu Asn Gln Ala Asp Leu Ser Leu Ala Leu Val
ATC CTG GAA AAC CAG GCA GAT CTA AGC TTG GCA CTG GCC GTC .........
                            BglII   HindIII
```

FIGURE 2B

```
                                                pMT11
       IL-1
Ile Leu Glu Asn Gln Ala Asp Leu Ser Phe Asn Ala Val Val Tyr His Ser
ATC CTG GAA AAC CAG GCA GAT CTA AGC TTT AAT GCG GTA GTT TAT CAC AGT TAA
                            BglII   HindIII
```

FIGURE 2C

```
                                       pMT11
       IL-1
Ile Leu Glu Asn Gln Ala
ATC CTG GAA AAC CAG GCA   TAAGCTTTAATGCGGTAGTTTATCACAGTTAA
                         HindIII
```

FIGURE 2D

```
                                                pMC1403
       IL-1
Ile Leu Glu Asn Gln Ala Asp Pro Val Val Leu Gln Arg
ATC CTG GAA AAC CAG GCA GAT CCC GTC GTT TTA CAA CGT .........
                            BglII/BamHI
```

```
EcoRI
GAATTCTCATGTTTACAGCTTATCTCGGAGCTGCATGTGTCAGAGCTTTCACCGTCATCACCGAAACGCG
         10        20        30        40        50        60        70 tacP
CAGGCAAGCTGTTGACAATTAATCATCGGCTCGTATAATGTGTGGAATTGTGAGCGGATAACAATTTCAC
         80        90       100       110       120       130       140

RBS                  Met Ser Ala Pro Phe Ser Phe Leu Ser Asn
ACAGGAAACAGGATCGTAAGGAGGTTTAAC             ATG TCT GCA CCG TTC AGC TTC CTG AGC AAC
         150       160       170                a   180 t   t           195     t

Val Lys Tyr Asn Phe Met Arg Ile Ile Lys Tyr Glu Phe Ile Leu Asn Asp Ala
GTA AAA TAC AAC TTC ATG CGT ATC ATC AAA TAC GAA TTT ATC CTG AAC GAC GCT
 g      210     t       a   g           230         c       245 t       c

ClaI
Leu Asn Gln Ser Ile Ile Arg Ala Asn Asp Gln Tyr Leu Thr Ala Ala Ala Leu
CTG AAC CAA TCG ATA ATC CGT GCT AAC GAC CAG TAC CTG ACT GCT GCT GCA CTG
 c   t       agt 270 t   a   c   t   t       290 c   g       300       tta His Asn Leu Asp Glu Ala Val Lys Phe Asp Met Gly Ala Tyr Lys Ser Ser Lys
CAC AAC CTG GAC GAA GCA GTA AAA TTT GAC ATG GGT GCT TAC AAA TCT TCT AAA
 t   t       t   325     g       335             345   · t   g   a   a   g MstI
Asp Asp Ala Lys Ile Thr Val Ile Leu Arg Ile Ser Lys Thr Gln Leu Tyr Val
GAT GAT GCT AAA ATC ACC GTG ATC CTG CGC ATC TCT AAA ACT CAG CTG TAC GTA
365                 t   380     t   a a a 395 a           a   t   t   g Thr Ala Gln Asp Glu Asp Gln Pro Val Leu Leu Lys Glu Met Pro Glu Ile Pro
ACT GCT CAG GAC GAA GAC CAG CCG GTA CTG CTG AAA GAA ATG CCG GAA ATC CCG
    420 c   a   t           a   a   g       450 g   g       t   g   a   c KpnI
Lys Thr Ile Thr Gly Ser Glu Thr Asn Leu Leu Phe Phe Trp Glu Thr His Gly
AAA ACC ATC ACT GGT TCT GAA ACC AAC CTG CTG TTC TTC TGG GAA ACT CAC GGT
            480 a       ag   g   495     c   c           510         520     c Thr Lys Asn Tyr Phe Thr Ser Val Ala His Pro Asn Leu Phe Ile Ala Thr Lys
ACC AAA AAC TAC TTC ACT TCT GTT GCT CAC CCG AAC CTG TTC ATC GCT ACT AAA
 t   g       t   540 a   a       c   t   a   560 t       t   t   c   a   g Gln Asp Tyr Trp Val Cys Leu Ala Gly Gly Pro Pro Ser Ile Thr Asp Phe Gln
CAG GAC TAC TGG GTT TGC CTG GCA GGT GGT CCG CCG TCT ATC ACT GAC TTC CAG
 a           590 g       t 600     g   g   a   c       620         t Ile Leu Glu Asn Gln Ala    ·
ATC CTG GAA AAC CAG GCA TAA
 a      640             g   g
```

GAATTCTCATGTTTACAGCTTATCTCGGAGCTGCATGTGTCAGAGCTTTCACCGTCATCACCGAAA
↑
EcoR1

CGGCGCAGGCAAGCTGTTGACAATTAATCATCGGCTCGTATAATGTGTGGAATTGTGAGCGGATAAC

AATTTCACACAGGAAACAGGATCGTAAGGAGGTTTAAC ATG AGC TCG CCC GGG GAT CCG
                                              ↑           ↑   ↑
                                             SstI        SmaI BamHI

TCG ACC TGC AGG CGG AGA ACT GGT AGG TAT GGA AGA TCT CTA GAA GCT TT
    ↑                                       ↑       ↑   ↑
   PstI                                   BglII    XbaI HindIII SalI
↑

FIGURE 7

TRUNCATED HUMAN INTERLEUKIN-A ALPHA

FIELD OF THE INVENTION

The invention relates generally to nucleotide sequences coding for human proteins, and more particularly to synthetic nucleotide sequences coding for the human immune system mediator, interleukin-1α (IL-1α).

BACKGROUND

The in vivo release of IL-1 from monocytes stimulated by exposure to bacteria or their products is pivotal to the generation of the acute-phase immune response following infection. The physiological and pathogenic responses of organs and tissues to IL-1 have been extensively reviewed, e.g. Dinarello, Rev. Infect. Dis., Vol. 6, pgs. 51–95 (1984). From an immunological standpoint, monocyte-derived IL-1 is crucial to host defense since triggering of both humoral and cell mediated branches of the immune system appear to be dependent upon its synthesis. IL-1 mediates a wide range of biological activities including stimulation of thymocyte proliferation via induction of interleukin-2 (IL-2) release, stimulation of B-lymphocyte maturation and proliferation, fibroblast growth factor activity and induction of acute-phase protein synthesis by hepatocytes. IL-1 has also been reported to stimulate prostaglandin and collagenase release from synovial cells, and to be identical to endogenous pyrogen, Krampschmidt, J. Leuk. Biol., Vol. 36, pgs. 341–355 (1984).

Biochemical and cDNA cloning studies have defined two related IL-1 proteins (α and β) that appear to have similar activities, March et al., "Cloning, Sequence and Expression of Two Distinct Human Interleukin-1 Complementary DNAs," Nature, Vol. 315, pgs. 641–647 (1985) and Gubler et al., "Recombinant Human Interleukin-1α: Purification and Biological Characterization," J. Immunol., Vol. 136, pgs. 2492–2497 (1986). The primary translation products of IL-1α and IL-1β mRNAs are, respectively, 271 and 269 amino acid proteins that do not encode typical transmembrane signal sequences (March et al., cited above). IL-1 appears to be a C-terminal 17,500 dalton fragment of the primary translation product, and expression of this fragment in E. coli produces a protein with properties apparently identical to the natural protein (March et al., and Gubler et al, cited above).

It is believed that IL-1, either alone or in combination with other lymphokines, has potential clinical applications, e.g. Sorg et al., Eds. Cellular and Molecular Biology of Lymphokines (Academic Press, New York, 1985). The development of a highly efficient bacterial expression system for IL-1 would increase its availability for medical and research applications, and the development of a rapid and convenient method of manipulating the amino acid sequence of native IL-1α would facilitate the development of useful IL-1α muteins.

SUMMARY OF THE INVENTION

Synthetic human interleukin-1α genes are provided whose codons are selected from those preferred by bacteria, particularly Escherichia coli (E. coli). High expression levels are obtained in an E. coli expression system for both native IL-1α and several mutant IL-1α's. The mutant IL-1α's comprise the N-terminal deletions of from 1 to 14 amino acids, and C-terminal additions of from 1 to 11 amino acids, with respect to the amino acid sequence of native human IL-1α.

The invention further includes a method for generating IL-1α muteins using the synthetic gene of the invention. The synthetic IL-1α gene is subdivided into segments by a series of unique restriction endonuclease sites (referred to herein as "unique restriction sites"). The number and spacing of the unique restriction sites are selected so that the gene segments between any two unique restriction sites can be conveniently replaced by segments having altered base sequence. A restriction site is unique in the sense that the synthetic gene and the vector into which the gene is inserted contain only one such restriction site, namely the one carried by the inserted synthetic gene. Preferably, the number and spacing of the unique restriction sites are such that replacement segments can be reliably synthesized using standard solid phase oligonucleotide synthesis techniques, e.g. on a commercially available automated DNA synthesizer. Shorter replacement segments reduce the probability of insertion and/or deletion changes upon cloning, and they make the task of sequence analysis easier because universal sequencing primers on small scale vector DNA preparations can be utilized. Preferably, the number and spacing of the unique restriction sites are selected so that the segments are from 40 to 180 bases in length.

Broadly, the method comprises the steps of (1) providing a synthetic IL-1α gene having a series of unique restriction sites with respect to an associated vector, the unique restriction sites being spaced from 40–180 bases apart along the synthetic IL-1α gene to form a plurality of segments; (2) replacing one or more segments with a replacement segment having a predetermined sequence to form a modified synthetic gene; (3) incorporating the associated vector containing the modified synthetic gene into a host; and (4) maintaining the host under conditions suitable for transcribing and translating the modified synthetic gene into a mutein.

The term "predetermined sequence" as used herein in reference to a replacement segment means that the replacement segment comprises a known sequence of bases determined beforehand by one employing the method. Preferably, the replacement segment is constructed by solid phase oligonucleotide synthesis. The replacement is effected by digestion of the synthetic gene by the two restriction endonucleases between whose restriction sites the replacement segment is to be placed. Thus, two fragments are formed upon such digestion: a fragment containing the bulk of the vector, and one or more connected segments. The two fragments are separated, and the vector-fragment is ligated with the replacement segment to form the associated vector containing the modified synthetic gene.

BRIEF DESCRIPTION OF THE DRAWINGS

FIGS. 1A–D illustrate DNA fragments used in the construction of a synthetic human IL-1α gene of the invention. Fragments are written as double stranded DNA (dsDNA) with appropriate protruding single stranded ends. Relevant restriction sites, or parts of restriction sites, are in bold type and are labelled above the site. Sizes of the lower strands are indicated below the sequences and lower case sequences are either vector sequence or sequences extraneous to the final expressed IL-1α construction.

FIGS. 2A–D illustrate the C-terminal IL-1α coding regions in various construction steps. The DNA sequence is presented as triplets with the corresponding amino acids indicated above. Relevant restriction sites are in bold type and are labelled below the DNA. The nature of each vector sequence to the 3' side of the C-terminal IL-1α encoding GCA triplet is indicated above the sequence.

FIG. 3 illustrates the DNA sequence of the completed and expressed synthetic human IL-1α gene. The coding region is arranged as triplets and corresponding amino acids are indicated. Relevant restriction sites are in bold type and are labelled above the sequence. The locations of the tacP promoter region and the ribosome-binding site (RBS) are indicated. The lower case letters under the sequence indicate neutral base changes found in the natural IL-1 sequence as a consequence of both the presence of new restriction sites and preferred codon usage. The two coding regions are 81% homologous. Eight non-bacterial-preferred codons are present in the synthetic coding region, these correspond to amino acids 23, 31, 32, 33, 55, 65, 66 and 71.

FIGS. 4A and 4B are representations of various expressed IL-1α synthetic genes and IL-1α-β-galactosidase genes. The black areas represent the 173 bp TAC-RBS regulatory region carrying the tacP promoter, the ribosome-binding site (RBS), and the initiator ATG triplet. The white regions are synthetic IL-1α coding sequences and the grey areas are other coding sequences. Relevant restriction sites are indicated by arrows.

DETAILED DESCRIPTION OF THE INVENTION

Synthetic genes for human interleukin-1α are provided which substantially comprise codons preferred by bacteria, particularly *E. coli*. Bacterial preferred codons are determined from a survey of sequenced bacterial genes provided by de Boer and Kastelein, in "Biased Codon Usage: An Exploration of its Role in Optimization of Translation," chapter 8, pgs. 225-283, Reznikoff and Gold, Eds., *Biotechnology Series* 1985. Table I below defines the bacterial preferred codons for use in accordance with the present invention. "Substantially comprising" in reference to the synthetic IL-1α genes means that some bacterial non-preferred codons may be used where necessary to facilitate the manipulation of segments of the synthetic genes with restriction endonucleases. Generally, it means 80-90 percent of the codons are bacterial preferred (as described more fully below). Standard abbreviations are used for designating amino acids, e.g. Lehninger, *Biochemistry*, 2nd Ed., pgs. 73-75 (Worth Publishers, New York, 1975), and the nucleoside bases (A=adenosine, G=guanosine, C=cytidine, T-thymidine, and U-uridine). Standard nomenclature for designating restriction endonucleases is used throughout, e.g. Roberts, pgs. 27-41, in Wu, Ed. *Methods in Enzymology*, Vol. 68 (Academic Press, New York, 1979).

TABLE I

| Bacterial Preferred Codons | |
|---|---|
| Amino Acid | Codon(s) |
| Leu | CUG |
| Arg | CGC |
| Gly | GGU |
|  | GGC |
|  | GGA |
|  | GGG |
| Ile | AUC |
| Tyr | UAC |
| His | CAC |
| Ser | UCU |
|  | UCC |
|  | AGC |
| Val | GUU |
|  | GUA |
| Pro | CCG |
|  | ACC |
| Gln | CAG |
| Asn | AAC |
| Lys | AAA |
| Asp | GAU |
|  | GAC |
| Glu | GAA |
| Cys | UGU |
|  | UGC |
| Phe | UUC |
| Trp | UGG |
| Met | AUG |
| Ala | GCU |
|  | GCA |

I. Bacterial Strains, Expression Vectors, and Recombinant DNA Protocols

Cloning and expression is carried out in standard bacterial systems, for example *E. coli* K-12 strain JM101 described by Vieira and Messing, *Gene*, Vol. 19, pgs. 259-268 (1982), which is commercially available. Expression vectors were purchased commercially (pUC12 from Pharmacia) or were constructed from commercially available vectors.

Restriction endonuclease digestions, DNA polymerase, kinase, ligase and exonuclease reactions were performed using standard techniques, e.g. Maniatis et al *Molecular Cloning: A Laboratory Manual* (Cold Spring Harbor Laboratory, New York, 1982). Enzymes are available from commercial sources, e.g. New England Biolabs or Boehringer Mannheim.

The alkaline method (Maniatis et al., cited above) was used for small scale plasmid preparations. For large scale preparations a modification of the alkaline method was used in which an equal volume of isopropanol was used to precipitate nucleic acids from the cleared lysate. Precipitation with cold 2.5M ammonium acetate was used to remove RNA prior to cesium chloride-ethidium bromide equilibrium density centrifugation.

For filter hybridizations Whatman 540 filter circles were used to lift colonies which were then lysed and fixed by successive treatments with 0.5M NaOH, 1.5M NaCl; 1M Tris.HCl pH8.0, 1.5M NaCl (2 min each); and heating at 80° C. (30 min). Hybridizations were in 6×SSPE, 20% formamide, 0.1% sodium dodecylsulphate (SDS), 100 µg/ml E. coli tRNA, 100 µg/ml Coomassie Brilliant Blue G-250 (Biorad) at 42° C. for 6 hrs using $^{32}$P-labelled (kinased) synthetic DNAs. (20×SSPE is prepared by dissolving 174 g of NaCl, 27.6 g of $NaH_2PO_4.H_2O$, and 7.4 g of EDTA in 800 ml of $H_2O$. pH is adjusted to 7.4 with NaOH, volume is adjusted to 1 liter, and sterilized by autoclaving).

Filters were washed twice (15 min, room temperature) with 1×SSPE, 0.1% SDS. After autoradiography (Fuji RX film), positive colonies were located by aligning the regrown colonies with the blue-stained colonies on the filters.

DNA was sequenced by either the chemical degradation method Maxam and Gilbert, *Methods in Enzymology*, Vol. 65, pg. 499 (1980), or by the dideoxy method, Sanger et al. *Proc. Natl. Acad. Sci.*, Vol. 74, pg. 5463 (1977). Templates for the dideoxy reactions were either single stranded DNAs of relevant regions recloned into M13 mp vectors, e.g. Messing et al. *Nucleic Acids Res.*, Vol. 9, pg. 309 (1981), or double-stranded DNA prepared by the minialkaline method and denatured with 0.2M NaOH (5 min, room temperature) and precipitated from 0.2M NaOH, 1.43M ammonium acetate by the addition of 2 volumes of ethanol. Dideoxy reactions were done at 42° C.

Figure 7:
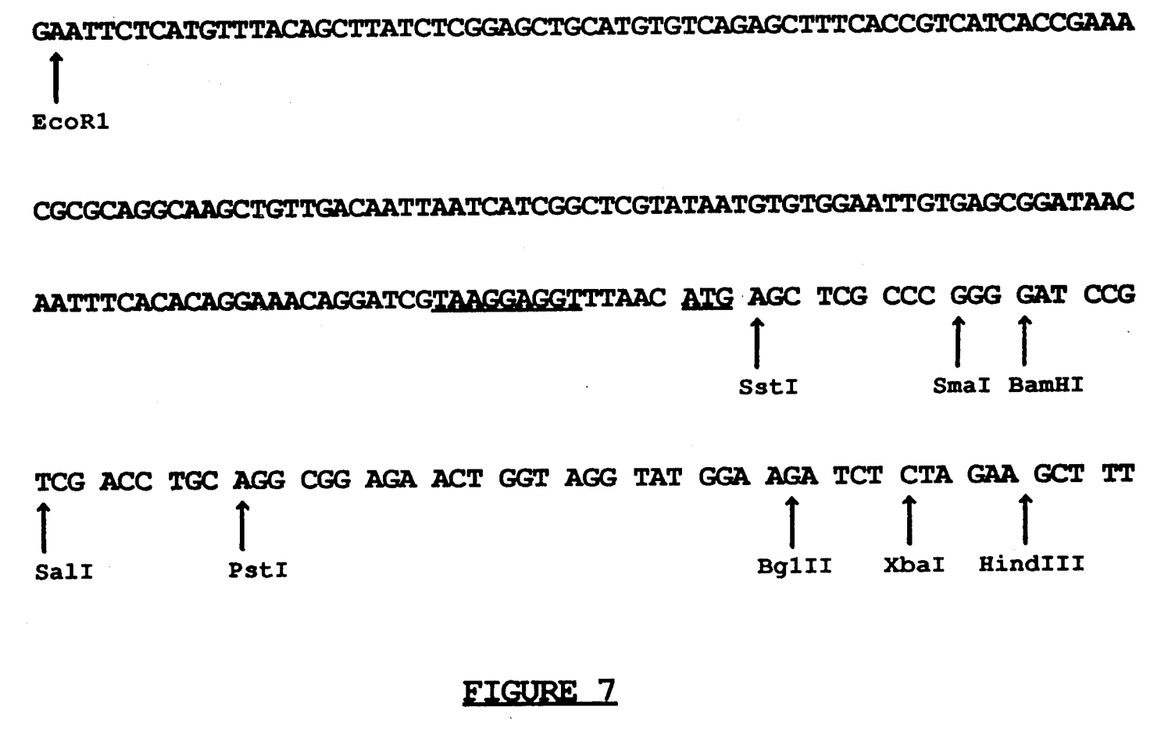
FIG. 7. Nucleotide sequences adjacent to the initiator ATG codon in the *E. coli* expression vector TAC-RBS. The sequences commence at an EcoR1 restriction site and ends with a HindIII site. Arrows indicate the 5' nucleotide after restriction by various nucleases which are indicated under the arrows. Ribosome binding sequence showing complementarity to the 3' end of 16S ribosomal RNA is shown in bold type and is underlined. ATG initiator codon is underlined.

The TAC-RBS vector was constructed by filling-in with DNA polymerase the single BamHI site of the tacP-bearing plasmid pDR540 (Pharmacia, PL). This was then ligated to unphosphorylated synthetic oligonucleotides (Pharmacia, PL) which form a double-stranded fragment encoding a consensus ribosome binding site (RBS, GTAAGGAGGTTTAAC). After ligation, the mixture was phosphorylated and religated with the SstI linker ATGAGCTCAT. This complex was then cleaved with SstI and EcoRI, and the 175 bp fragment isolated via polyacrylamide gel electrophoresis (PAGE) and cloned into EcoRI-SstI restricted pUC12 (Pharmacia, PL). One clone with the correct sequence was selected and the 180 bp EcoRI-BamHI tacP-RBS fragment was recloned into pMT11hc. pMT11hc is a small (2.3 kb), high copy, $AMP^R$, $TET^S$ derivative of pBR322 that bears the πVX plasmid EcoRI-HindIII polylinker region. The sequence of the RBS-ATG-polylinker regions of the final construction (called TAC-RBS) is shown in FIG. 7.

II. DNA Syntheses And Cloning

DNA was synthesized by phosphoramidite chemistry using Applied Biosystems 380A synthesizers. Synthesis, deprotection, cleavage and purification (7M urea PAGE, elution, DEAE-cellulose chromatography) were done as described in the 380A synthesizer manual. Complementary strands of synthetic DNAs to be cloned (400 ng each) were mixed and phosphorylated with polynucleotide kinase in a reaction volume of 50 µl. This DNA was ligated with 1 µg of vector DNA digested with appropriate restriction enzymes, and ligations were in a volume of 50 µl at room temperature for 4 to 12 hours. Conditions for phosphorylation, restriction enzyme digestions, polymerase reactions, and ligation have been described (Maniatis et al., cited above). Colonies were scored for lacZ+ by plating on L agar supplemented with ampicillin, isopropyl-1-thio-beta-D-galactoside (IPTG) (0.4 mM) and 5-bromo-4-chloro-3-indoyl-beta-D-galactopyranoside (x-gal) (40 µg/ml). When natural DNA fragments were used in clonings, 20 µg of plasmid was digested and the products separated by preparative 6% PAGE (Maxam and Gilbert, cited above) and further purified via DEAE-cellulose chromotography (Maniatis et al., cited above). One-tenth of the fragment was ligated with 1 µg of vector DNA digested with appropriate restriction enzymes.

III. Preparation of Protein Extracts and Bioassays of Human IL-1α

Single colonies were picked into 0.2 ml of L broth (described in Maniatis et al., cited above) with 100 µg/ml ampicillin and grown at 37° C. overnight without shaking. A further 2 mls of medium was added and the cells were grown with shaking at 37° C. for 6 hrs. Cells harboring the TAC-derived plasmids were induced by the addition of 04.mM IPTG (Sigma) after 2 hrs of growth. Cells were harvested by centrifugation (13,000 rpm, 2 min, Biofuge A), resuspended in 1 ml of phosphate-buffered saline (PBS, Sigma) with 1 mM phenylmethylsulfonyl fluoride (PMSF) (Sigma) and sonicated for 40 pulses (50%) at 40 watts using the miniprobe of the Branson Cell Disruptor 200. Following the addition of 100 µl of 10% SDS (Biorad) and incubation at 37° C. for 15 min, the samples were centrifuged (13,000 rpm, 15 min, Biofuge A). Dilutions of the samples are bioassayed by several available methods. For example, IL-1α can be assayed by thymocyte costimulation, Mizel and Mizel, *J. Immunol.*, Vol. 126, pg. 834 (1981). Preferably, IL-1α is assayed by the IL-1 responsive T-cells, such as the IA5 clone of the lymphoma LBRM33, deposited with the American Type Culture Collection (ATCC), Rockville, Md., under ATCC accession number CRL8079, and described in Gillis and Mizel, *Proc. Natl. Acad. Sci*, vol. 78, pg. 1133 (1981), and in U.S. Pat. No. 4,404,280 (the U.S. patent being incorporated by reference for its description of the bioassay and the lymphoma LBRM33 clone IA5). This latter assay is referred to herein as the "IA5 conversion assay."

IV. Construction of a Synthetic Human IL-1α Gene

Figure 1A:
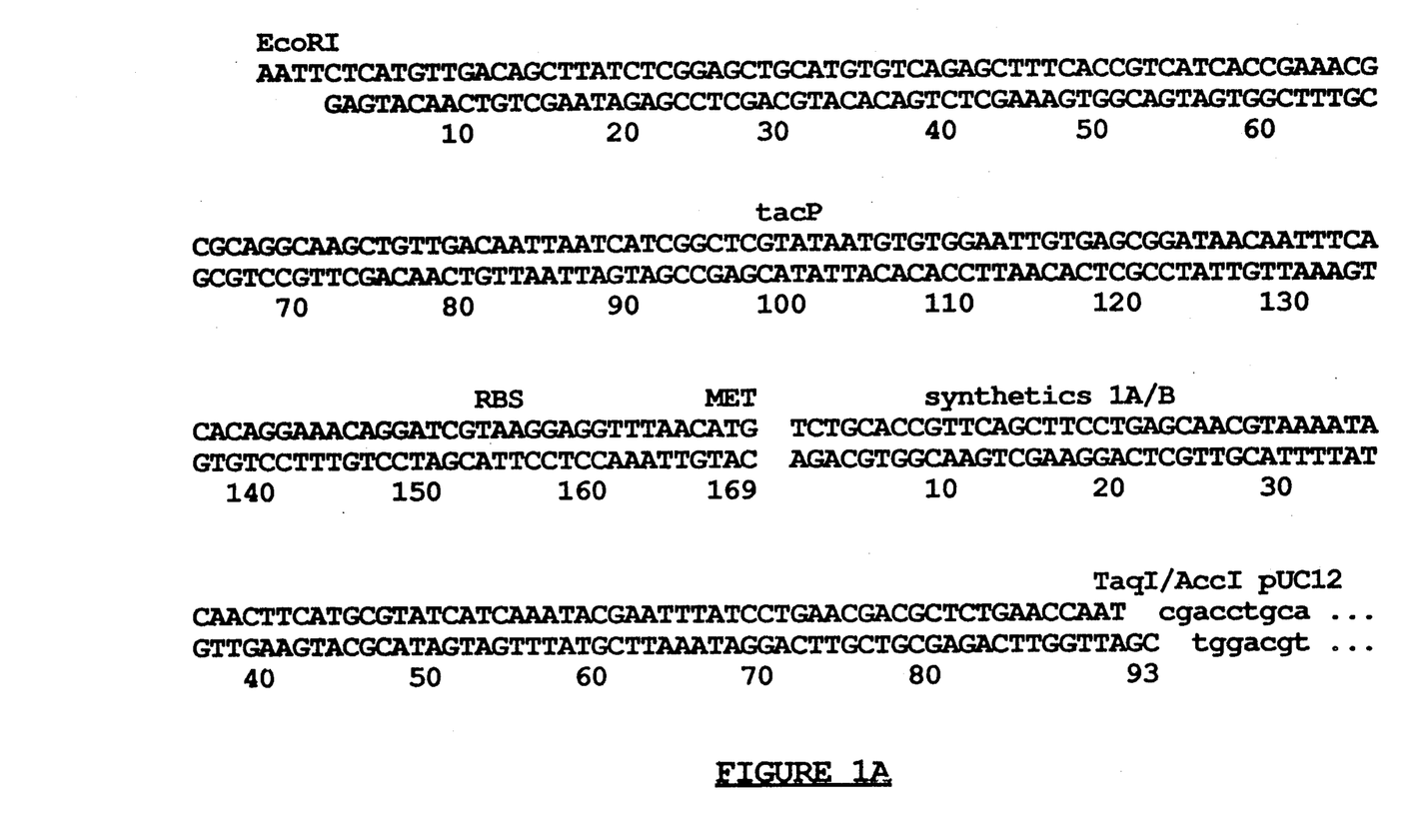

The scheme used for synthesis and cloning of the active C-terminal region of human IL-1α proceeded in steps that utilized eight synthetic double stranded DNA (dsDNA) fragments. In Step 1, a 93 bp synthetic dsDNA fragment (1A/B, FIG. 1A) encoding the N-terminal part of the IL-1α region to be expressed was cloned into the E. coli expression vector TAC-RBS. This vector is a pUC12 derivative that carries the tac promoter upstream from a consensus ribosome binding site. The initiator ATG codon overlaps with a unique Sst1 restriction site such that treatment with Sst1 and T4 DNA polymerase generates a flush end at the TAC-RBS ATG codon. Downstream from this ATG codon follows the pUC12 polylinker sequence. Synthetics 1A/B were cloned into TAC-RBS vector treated as above then restricted with AccI to accommodate the overlapping CG residues at the distal end of 1A/B (FIG. 1A).

In Step 2, dsDNA synthetic fragments 7A/B and 8A/B were mixed and cloned into pUC12 vector DNA restricted with SalI and HindIII. Fragments 7A/B and 8A/B have complementary 9 residue single-stranded ends, as well as single-stranded ends to fit, respectively, SalI and HindIII restricted DNA (FIG. 1D). Fragment 7A/B has a KpnI site at positions 3→8 (FIG. 1D) that is part of the IL-1α coding region and is preceded by the TCGAC sequence that completes the SalI restriction site. The additional C residue proximal to the KpnI restriction site brings the IL-1α coding region into frame with the lacZα' coding region of pUC12. Fragment 8A/B has an in-phase BglII restriction site immediately distal to its IL-1α coding region and proximal to the sequence that completes the HindIII restriction site (FIG. 1D). Since this synthetic region displaces the PstI restriction site in the pUC12 vector, the vector background was lowered by treating the ligation with PstI prior to transformation.

Figure 1B:
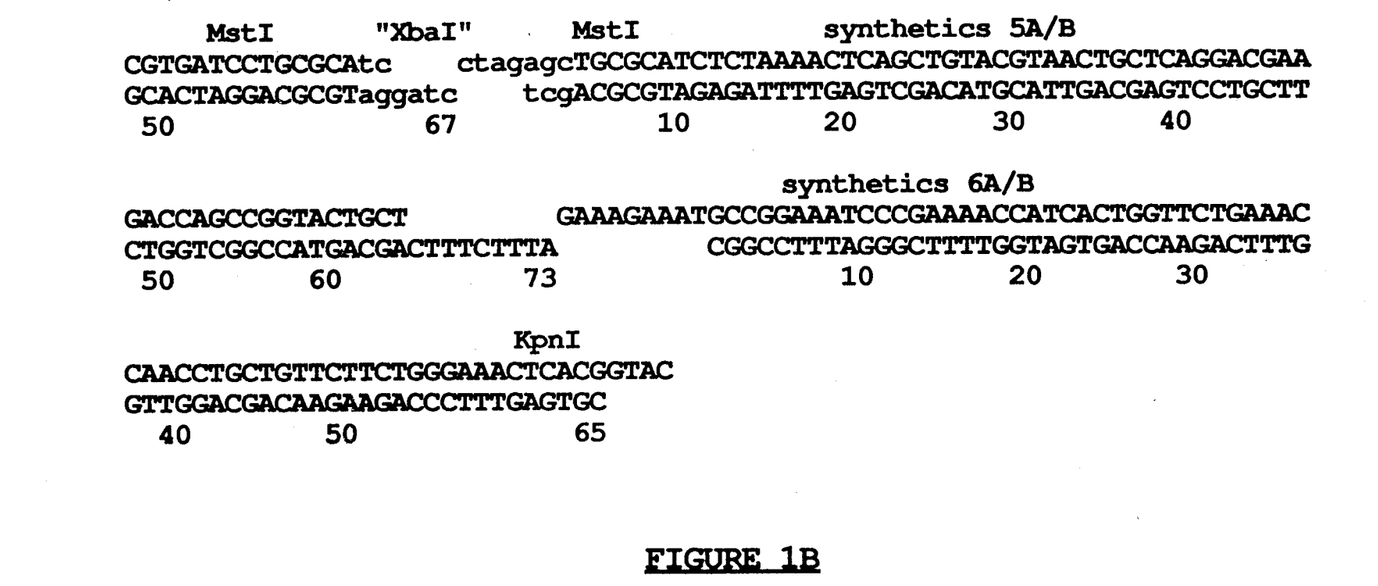

In Step 3, synthetic dsDNA fragments 5A/B and 6A/B were cloned into XbaI and KpnI-restricted completed Step 2 DNA (FIG. 1B). Fragment 5A/B has a MstI restriction site at the 5' end of its IL-1α coding region preceded by a sequence to fit XbaI-restricted DNA, as well as additional residues to maintain the IL-1α coding residue in-phase with the lacZα' coding region. (Casadaban and Cohen, in *J. Mol. Biol.*, Vol. 138, pg. 179 (1980) describe E. coli strains with the so-called lacZM15 deletion, whose F episome produced beta-galactosidase is intercistronically complemented by the α segment of beta-galactosidase coded by the lacZα' of a vector). Fragment 6A/B has a 9 residue protruding 5' end complimentary to a protruding 5' end on fragment 5A/B, as well as a GTAC protruding 3' end to fit KpnI-restricted DNA. Since this synthetic DNA displaces the SalI site in completed Step 2 DNA, the ligation was treated with SalI prior to transformation to reduce the background.

Figure 1C:
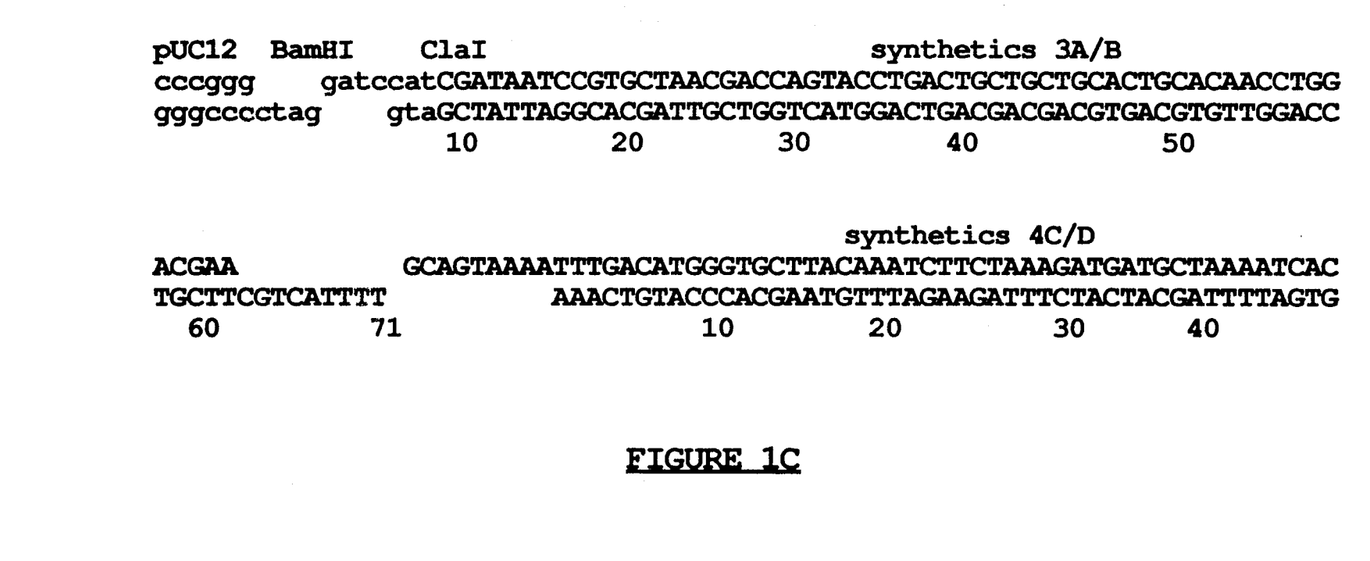
Figure 1D:
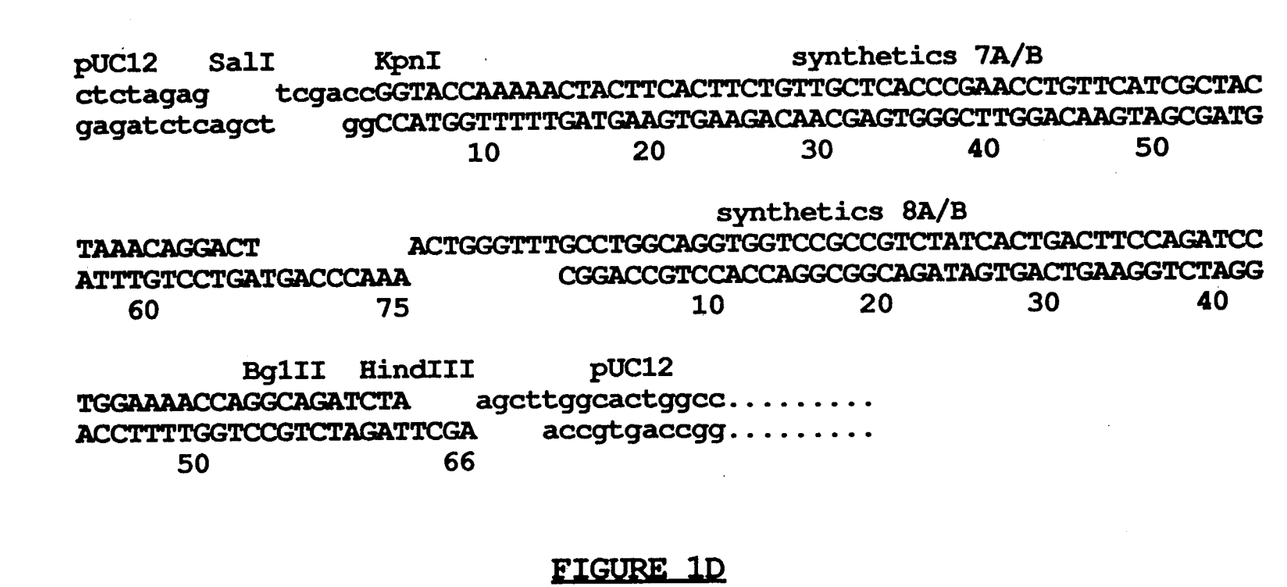

In Step 4, synthetic dsDNA fragments 3A/B and 4C/D (FIG. 1C) were cloned into BamHI and XbaI-restricted completed Step 3 DNA. Fragment 3A/B has a ClaI restriction site at the 5' end of its IL-1α coding region preceded by a 5' protruding GATC sequence to fit BamHI-restricted DNA. The C residue proximal to the ClaI restriction site serves to maintain the IL-1α reading frame in-phase with that of lacZα'. Fragment 4C/D has a 5' single stranded 9 residue end that is complementary to a similar end of fragment 3A/B (FIG. 1B). The distal end of fragment 4C/D includes a CTAG 5' protruding end that fits XbaI-restricted DNA and two residues of non-IL-1α coding sequence that maintain the reading frame. Since the Step 5 cloning does not restore an XbaI restriction site, the ligation reaction was treated with XbaI prior to transformation to lower background.

In Step 5, the 265 bp EcoRI-TaqI fragment from completed Step 1 DNA (FIG. 1A) was cloned into EcoRI and ClaI-restricted completed Step 4 DNA. This step completed assembly of synthetic IL-1α DNAs.

Figure 2A:
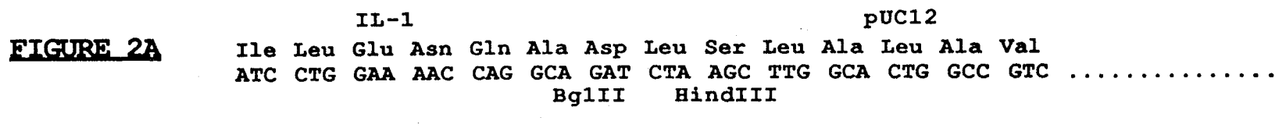
Figure 2B:
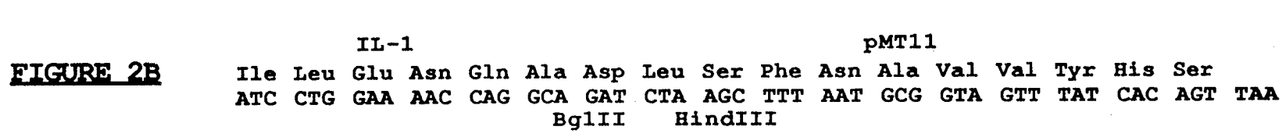

In Step 6, the 656 bp EcoRI-HindIII fragment from completed step 5 DNA was cloned into EcoRI and HindIII restricted vector pMT11hc DNA. The vector was changed from TAC-RBS to pMT11hc to preserve the uniqueness of the ClaI, MstI, and KpnI sites. A different choice of vectors could eliminate the need for this step. pMT11hc is a multicopy plasmid vector which has a sequence distal to the HindIII restriction site that terminates the IL-1α coding region 12 codons distal to the GCA that encodes the C-terminus of IL-1α. The sequence of the C-terminal IL-1α coding region in Step 6 DNA is shown in FIG. 2B.

In Step 7, the 15 bp in-frame insertion at the IL-1α MstI restriction site (FIG. 1B) was removed by restricting completed Step 6 DNA with MstI and religating.

Figure 2C:
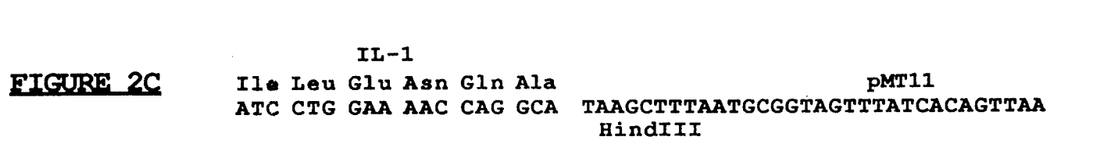

In Step 8, a TAA translation termination codon was placed immediately distal to the C-terminal GCA codon by restricting completed Step 7 DNA with BglII, treating with mung bean nuclease, and religating (FIG. 2C). The sequence of the completed synthetic IL-1α gene is shown in FIG. 3.

Figure 4A:
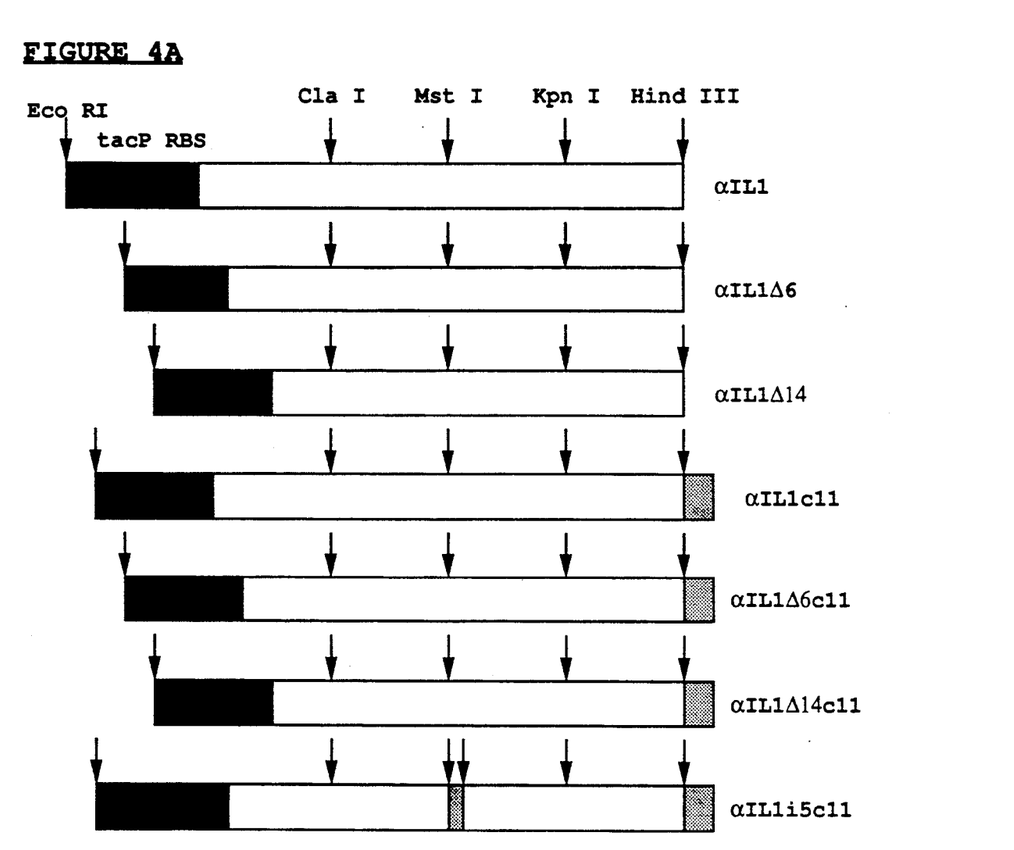
FIG. 4A illustrates the seven final expression constructions, all of which are present in the pMT11hc vector.
Figure 4B:
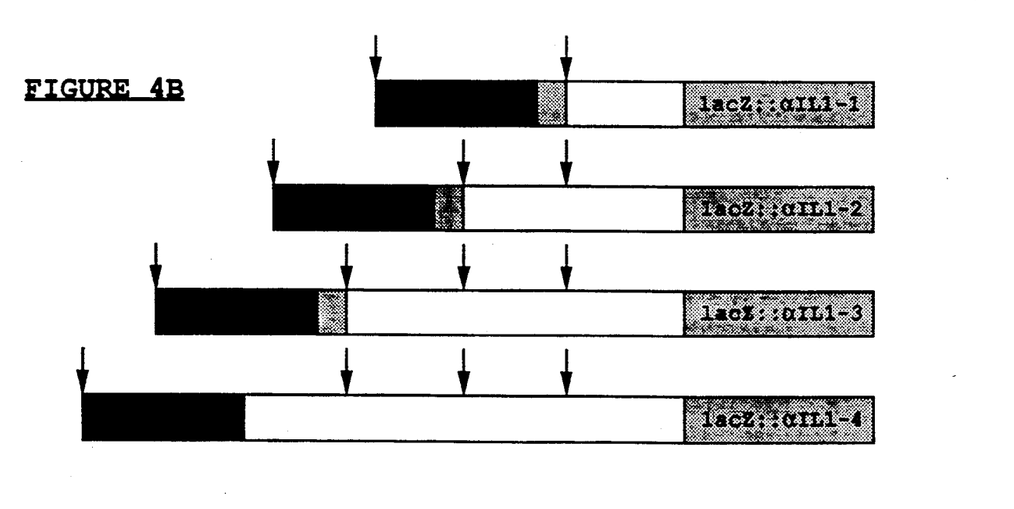
FIG. 4B illustrates the four IL-1α-β-galactosidase fusion expression plasmids, all of which are present in the pMC1403 vector.

Amongst transformants from Step 1 that were characterized by DNA sequence analysis, two were found to have, respectively, 6 and 14 codons deleted in the N-terminal coding region. These two deletion coding regions were carried forward to Steps 6 through 8 in parallel with the expected Step 1 DNA. FIG. 4 shows graphically the 7 different IL-1α coding regions that were constructed, representing combinations of N-terminal sequences, MstI-insertion, and 11 codon C-terminal additions.

Figure 5:
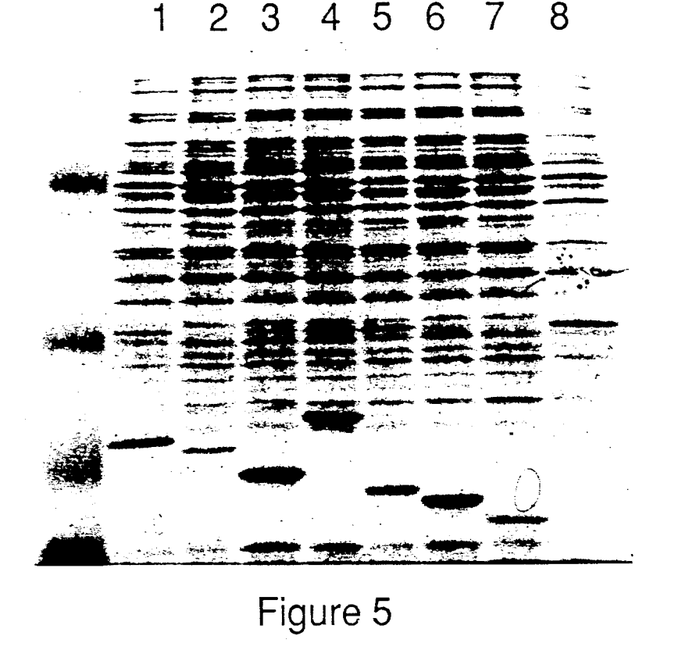
FIG. 5 illustrates the results of protein PAGE (15%) analysis of SDS-extracted proteins of JM101 cells bearing various IL-1α expression plasmids. Tracks 1 through 8 represent, respectively, αIL1c11, αIL1Δ6c11, αIL1Δ14c11, αIL1i5c11, αIL1, αIL1Δ6 αIL1Δ14 and TAC ex IL-2. The $M_r$ markers shown on the left are: Ovalbumm, 43,000; α-Chymotrypsinogen, 25,700; β-lactoglobulin, 18,400; lysozyme, 14,300.

The seven IL-1α expression plasmids represented in FIG. 4A were transformed into E. coli strain JM101. Protein extracts of such cells were subjected to PAGE (as described by Laemmli, *Nature*, Vol. 227, pg. 680 [1970]) and visualized by Coomassie Blue straining. As shown in FIG. 5, each plasmid directed abundant synthesis of the relevant IL-1α polypeptide. For example, we estimated by densitometer scanning that 6% of the total protein synthesized by the αIL1-bearing strain is IL-1α polypeptide. Dilutions of these extracts were tested for IL-1 activity using the IA5 conversion assay, which measures the capacity of IL-1 to stimulate IL-2 release from a mitogen-stimulated cloned murine lymphoma cell line (Gillia and Mizel, cited above). All protein extracts, except that from the αIl1i5c11 plasmid-bearing strain (this plasmid contained the MstI fragment, which was excised from the other plasmids in step 7), had high levels of IL-1 activity ($10^4$–$10^6$ units/ml) and the levels between the active extracts were identical within experimental error (2-fold).

Figure 2D:
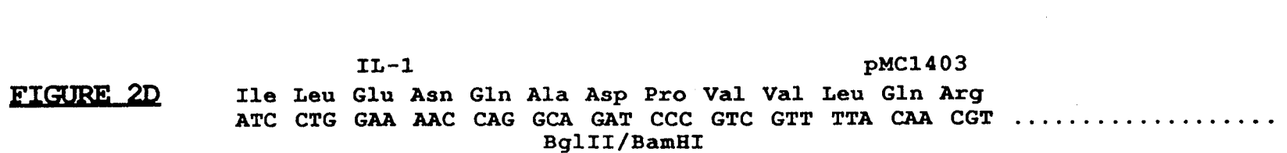
Figure 6:
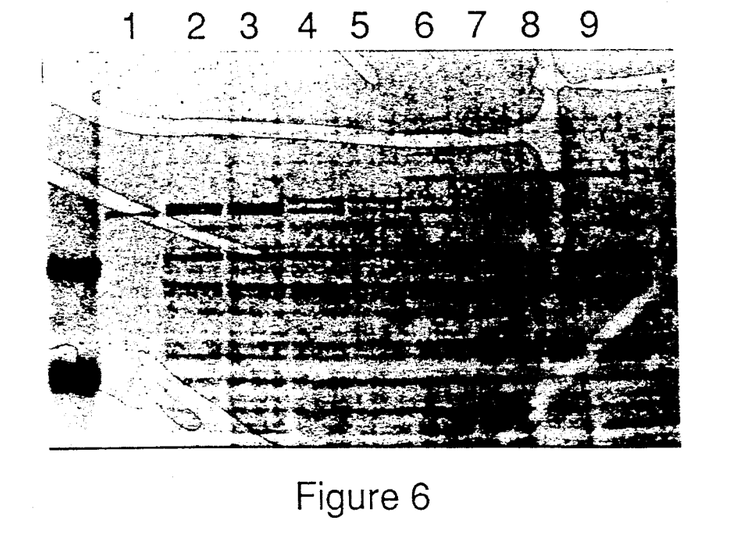
FIG. 6 illustrates the results of protein PAGE (5%) analysis of SDS-extracted proteins of JM101 cells bearing various IL-1α-β-galactosidase expression plasmids. 1, pure β-galactosidase; 2, 3, lacZ::αIL1-1; 4, 5, lacZ-::αIL1-2; 6, 7, lacZ::αIL1-3; 8, 9, lacZ::αIl1-4 $M_r$ markers shown on the left are Myosin (H-chain), 200,000; Phosphorylase B, 92,500; Bovine serum albumin, 68,000.

The BglII restriction site immediately distal to the C-terminal IL-1α GCA codon in completed Step 7 DNA is in-phase with the unique BamHI restriction site at the N-terminus of the lacZ coding region of the plasmid pMC1403 (Casadaban et al., cited above and FIG. 2D). The 651 bp EcoRI-BglII fragment from completed Step 7 DNA was cloned into EcoRI and BamHI restricted DNA. This places the entire IL-1α coding region proximal to the N-terminal coding region of lacZ. The identity of the IL-1 and lacZα' reading frames during assembly of the synthetic gene permitted construction of three further IL-1α-β-galactosidase fusion protein expression plasmids. The 176 bp EcoRI-SstI tacP DNA fragment from the TAC-RBS vector (FIG. 1A) was ligated together with SstI-BglII fragments from, respectively, completed Steps 2 and 3 DNAs, completed Step 4 DNA deleted for the 15 bp MstI insert, and EcoRI and BamHI-restricted pMC1403 DNA. Transformation of this ligation reaction into JM101 permitted the detection on x-gal and IPTG-containing L-ampicillin plates of plasmids expressing defined amounts of IL-1α sequence at the N-terminus of β-galactosidase. The four such expression plasmids that we constructed are represented in FIG. 4B. Extracts of E. coli strain JM101 bearing these 4 plasmids were analyzed by PAGE and the proteins were visualized by Coomassie Blue staining. FIG. 6 shows that each strain synthesized abundant amounts of IL-1α-β-galactosidase fusion protein. These extracts were inactive in the IL-1 1A5 conversion assay.

The foregoing description of the preferred embodiments and examples of the subject invention have been presented for purposes of illustration and description and for a better understanding of the invention. They are not intended to be exhaustive or to limit the invention to the precise forms disclosed; and obviously, many modifications and variations are possible in light of the above teaching. The particular examples were chosen and described in some detail to best explain the principles of the invention and its practical application to thereby enable others skilled in the relevant art to best utilize the invention in various embodiments and with various modifications as are suited to the particular use contemplated. It is intended that the invention be defined by the claims appended hereto.

We claim:

1. A mutant human interleukin-1α polypeptide defined by the formula:

Met—Arg—Ile—Ile—Lys—Tyr—Glu—Phe—

Ile—Leu—Asn—Asp—Ala—Leu—Asn—Gln—

Ser—Ile—Ile—Arg—Ala—Asn—Asp—Gln—

Tyr—Leu—Thr—Ala—Ala—Ala—Leu—His—

Asn—Leu—Asp—Glu—Ala—Val—Lys—Phe—

Asp—Met—Gly—Ala—Tyr—Lys—Ser—Ser—

Lys—Asp—Asp—Ala—Lys—Ile—Thr—Val—

Ile—Leu—Arg—Ile—Ser—Lys—Thr—Gln—

Leu—Tyr—Val—Thr—Ala—Gln—Asp—Glu—

Asp—Gln—Pro—Val—Leu—Leu—Lys—Glu—

Met—Pro—Glu—Ile—Pro—Lys—Thr—Ile—

Thr—Gly—Ser—Glu—Thr—Asn—Leu—Leu—

Phe—Phe—Trp—Glu—Thr—His—Gly—Thr—

Lys—Asn—Tyr—Phe—Thr—Ser—Val—Ala—

His—Pro—Asn—Leu—Phe—Ile—Ala—Thr—

Lys—Gln—Asp—Tyr—Trp—Val—Cys—Leu—

Ala—Gly—Gly—Pro—Pro—Ser—Ile—Thr—

Asp—Phe—Gln—Ile—Leu—Glu—Asn—Gln—

Ala.

* * * * *